United States Patent [19]

Utsumi et al.

[11] Patent Number: 5,258,160
[45] Date of Patent: Nov. 2, 1993

[54] PROCESS AND APPARATUS FOR PRODUCING ELONGATED BODY OF ELASTIC MODULUS CHANGING TYPE

[75] Inventors: Atsushi Utsumi, Itami; Masaaki Ohtsuji, Amagasaki; Motohiko Yamasaki, Amagasaki; Tamotsu Kaide, Amagasaki, all of Japan; Kazuo Onishi, New York, N.Y.

[73] Assignee: Mitsubishi Cable Industries, Ltd., Amagasaki, Japan

[21] Appl. No.: 927,859

[22] Filed: Aug. 11, 1992

[30] Foreign Application Priority Data

Aug. 21, 1991 [JP] Japan .................. 3-234156

[51] Int. Cl.⁵ .................................. B29C 47/92
[52] U.S. Cl. .................... 264/558; 264/40.3; 264/40.7; 264/570; 264/167; 264/173; 264/209.8; 425/97; 425/113; 425/131.1; 425/132; 425/145; 425/326.1; 425/462
[58] Field of Search ................ 264/557–569, 264/570, 514, 173, 167, 150, 149, 40.3, 40.7, 209.8; 425/94, 97, 98, 107, 113, 145, 461, 462, 133.1, 132, 131.1, 326.1

[56] References Cited

U.S. PATENT DOCUMENTS

| | | | |
|---|---|---|---|
| 2,620,515 | 12/1952 | Olson | 264/560 |
| 3,724,985 | 4/1973 | Burlis et al. | |
| 3,752,617 | 8/1973 | Burlis et al. | 425/145 |
| 3,928,525 | 12/1975 | Fuwa et al. | |
| 4,056,344 | 11/1977 | Lemelson | |
| 4,091,064 | 5/1978 | Kakinuma et al. | 264/174 |
| 4,198,363 | 4/1980 | Noel | |
| 4,211,741 | 7/1980 | Ostoich | 264/173 |
| 4,276,250 | 6/1981 | Satchell et al. | 425/132 |
| 4,394,338 | 7/1983 | Fuwa | 264/174 |
| 4,636,346 | 1/1987 | Gold et al. | 264/150 |
| 4,753,765 | 6/1988 | Pande | 264/150 |
| 4,888,146 | 12/1989 | Dandereau | 264/173 |
| 4,904,431 | 2/1990 | O'Maleki | 264/150 |
| 5,059,375 | 10/1991 | Lindsay | 264/173 |

FOREIGN PATENT DOCUMENTS

| | | |
|---|---|---|
| 0294337 | 12/1988 | European Pat. Off. |
| 032869 | 4/1992 | Fed. Rep. of Germany |
| 54-008036 | 4/1979 | Japan |
| 54-8036 | 4/1979 | Japan |
| 2-30265 | 7/1990 | Japan |
| WO8803421 | 5/1988 | PCT Int'l Appl. |

OTHER PUBLICATIONS

Week 9122, Derwent Publications, Ltd., London, GB; AN 91-159193 & JP-A 3 093 523 (Mitsubishi Cable Ind. Ltd.) Apr. 18, 1991.
Week 8002, Derwent Publications Ltd., London, GB; AN 80-02779 & JP-A 54 151 614 (Nippon Zeon K.K.) Dec. 29, 1979.

Primary Examiner—Jeffery Thurlow
Attorney, Agent, or Firm—Armstrong, Westerman, Hattori, McLeland & Naughton

[57] ABSTRACT

A process and apparatus for producing an elongated body changing in elastic modulus longitudinally thereof with use of polymers without resulting in variations in the outside and inside diameters of the body even when the polymers are different in extrusion characteristics or swelling characteristics. The apparatus may include a feeder 1 for extruding a first polymer in a molten state and a feeder 2 for extruding a second polymer, which is different from the first polymer in elastic modulus and similarly in a molten state. The feeders alternately discharge the respective polymers, which are continuously fed to a long-land die 5 along with a lubricant supplied from a lubricant applicator 4. The polymers are formed into the desired shape and cooled in the die 5, and thereafter extruded.

17 Claims, 4 Drawing Sheets

FIG. 3(a)
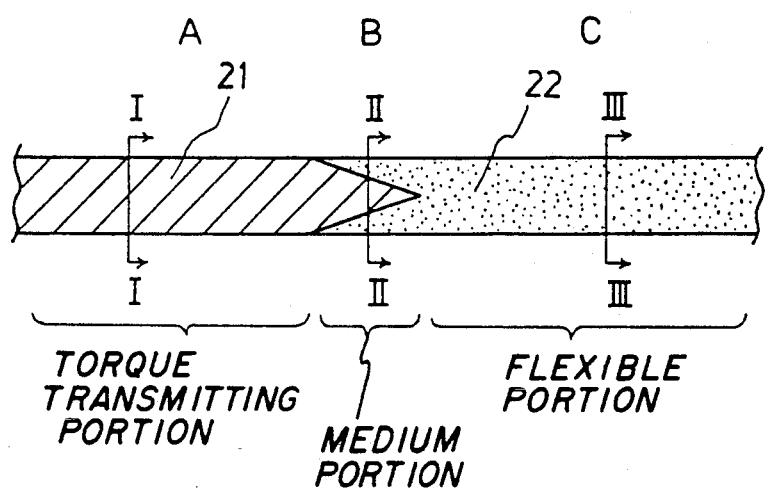
FIG. 3(b)          FIG.3(d)
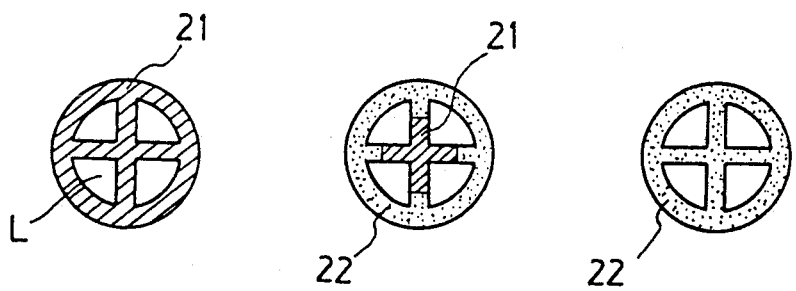
FIG.3(c)

FIG. 4(a)
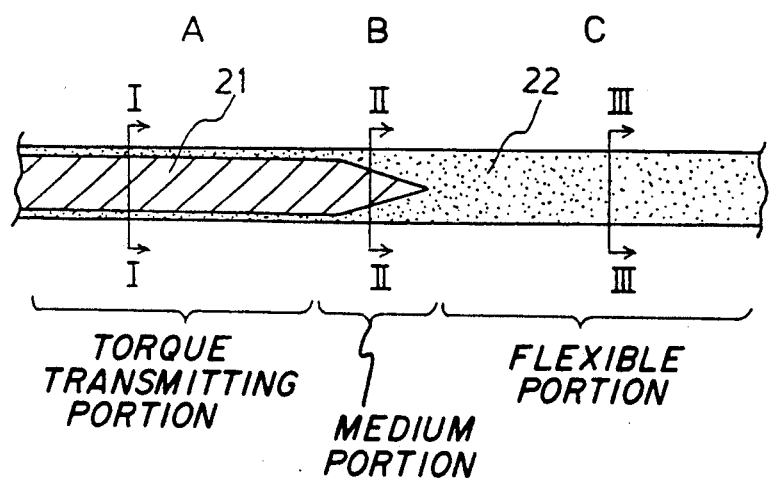
FIG. 4(b)
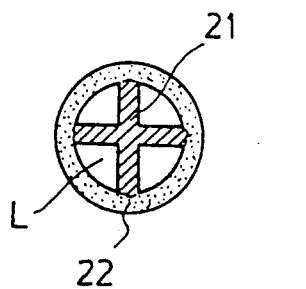
FIG. 4(c)
FIG. 4(d)
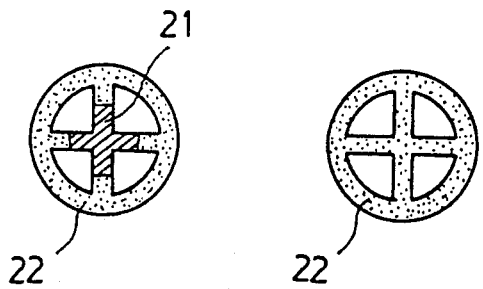

PROCESS AND APPARATUS FOR PRODUCING ELONGATED BODY OF ELASTIC MODULUS CHANGING TYPE

BACKGROUND OF THE INVENTION

1. Field of the Invention

The present invention relates to a process and an apparatus for continuously producing elongated bodies changing in elastic modulus longitudinally thereof, such as elongated bodies having an elastic modulus changing stepwise longitudinally thereof, those having a portion with an elastic modulus changing not stepwise but gently, or those having an elastic modulus continuously changing longitudinally thereof.

2. Description of the Prior Art

Elongated bodies of the elastic modulus changing type are suited, for example, for use as catheters which are inserted into the human body or animal bodies for therapeutic or diagnostic purposes. It is required that the catheter be easily insertable into the body, unlikely to damage or injure body tissues and adapted for such torque transmission that when the catheter as inserted in the body is rotated at its base end portion, the forward end thereof is also rotatable with the base end portion. These requirements can be fulfilled if the catheter comprises a flexible forward end portion having appropriate flexibility and elastic modulus, and a base end portion serving as a torque transmitting portion and having rigidity suited to torque transmission. When thus adapted to have varying elastic moduli, elongated bodies of the type mentioned can be used suitably as catheters.

Elongated bodies which change in elastic modulus longitudinally thereof are produced, for example, by a process wherein elongated bodies different in elastic modulus and each having a desired length are joined together end-to-end with adhesive, or fused to each other end-to-end by heating. However, such a method has the drawback that the resulting body becomes altered in outside diameter or reduced in mechanical strength at the joint, and requires much labor for the joining work. Especially when hollow elongated bodies are to be joined to each other, increased difficulty is encountered in joining the bodies without blocking or deforming the hollow channel.

Examined Japanese Patent Publication SHO 54-8036 (1979) discloses a process for producing a "slender plastics tube for medical use," i.e., an extrusion process for continuously producing an elongated body varying in physical properties longitudinally thereof, wherein two kinds of polymer materials which are different in physical properties are alternately fed to a mixing die from respective extruders. Nevertheless, when different polymer materials are merely fed to the mixing die alternately for extrusion as in the disclosed process, there arises the problem that the resulting elongated body varies in outside diameter and in inside diameter longitudinally thereof since the polymers of different physical properties differ in extrusion characteristics and in swelling characteristics.

SUMMARY OF THE INVENTION

An object of the present invention is to provide a process and an apparatus for producing an elongated body changing in elastic modulus longitudinally thereof without necessitating a cumbersome joining procedure of adhesive or thermal bonding and without resulting in variations in the outside and inside diameters of the body even when the polymers used are different in extrusion characteristics or swelling characteristics.

More specifically, the present invention provides a process for producing an elongated body of the elastic modulus changing type characterized by continuously feeding at least two kinds of polymers different in elastic modulus alternately to a long-land die having an inner surface supplied with a lubricant, preferably feeding in addition to the polymers a skin layer polymer continuously to the outermost layer of the charge within the die, forming and cooling the charge within the long-land die and extruding the cooled charge. The invention further provides a production apparatus characterized in that the apparatus comprises means for feeding at least two kinds of polymers different in elastic modulus, a long-land die connected to each of the polymer feeding means and having a forming zone and a cooling zone, and means for supplying a lubricant to the inner surface of the long-land die.

BRIEF DESCRIPTION OF THE DRAWINGS

FIG. 3, (a) is a view in longitudinal section of a catheter of the elastic modulus changing type obtained by feeding polymers to a long-land die in a completely replacing mode, FIG. 3, (b) to (d) being views in section taken respectively along the line I—I, the line II—II and the line III—III in FIG. 3, (a); and FIG. 4, (a) is a view in longitudinal section of a catheter of the elastic modulus changing type obtained by feeding polymers to a long-land die in a partly replacing mode, FIG. 4, (b) to (d) being views in section taken respectively along the line I—I, the line II—II and the line III—III in FIG. 4, (a).

DETAILED DESCRIPTION OF THE INVENTION

Figure 1:
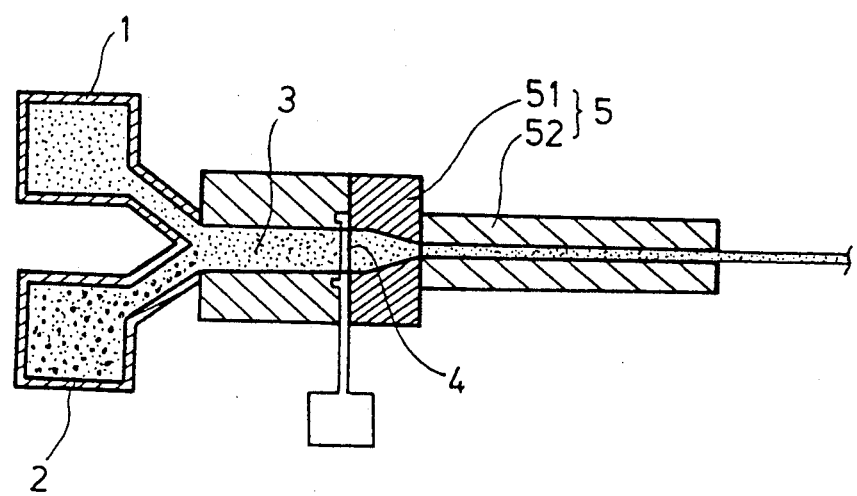
FIG. 1 is a diagram in section showing an example of apparatus for practicing the process of the invention for producing an elongated body of the elastic modulus changing type.

FIG. 1 is a sectional view schematically showing an example of apparatus of the invention. With reference to the drawing, the production process and apparatus embodying the invention will be described. The illustrated example is adapted to produce elongated bodies of the elastic modulus changing type by alternately feeding two kinds of polymers which are different in elastic modulus. Serving as the means for feeding these polymers are a first polymer feeder 1 and a second polymer feeder 2, the polymer outlets of which are connected to a long-land die 5. The inner surface of the die 5 is covered with a lubricant discharged from a lubricant applicator 4. The polymers are continuously fed to the die 5, formed and cooled, and thereafter extruded from the die.

More specifically, the feeder 1 for feeding one of the polymers, i.e., first polymer, in a molten state, and the feeder 2 for feeding the other polymer, i.e., second polymer which differs from the first polymer in elastic modulus, similarly in a molten state alternately discharge the respective polymers, which are continuously fed to the long-land die 5 along with the lubricant supplied from the lubricant applicator 4. When required, a confluent portion 3 is provided where the polymers discharged from the respective feeders join together and which serves as a common channel for the combined polymers to flow therethrough into the long-land die 5. The polymers are formed into the desired shape and cooled within the long-land die 5, and thereafter extruded therefrom.

With the process described above, the different polymers are not merely extruded alternately but alternately continuously fed to the long-land die, in other words, into a relatively long closed channel, in which the polymers are formed into the desired shape and cooled, and the polymers are thereafter extruded as generally solidified in shape. Accordingly, the polymer materials, even if different in extrusion characteristics or swelling characteristics, can be extruded into an elongated body of uniform outside diameter.

While at least two polymer feeders may be used, the outlet of each feeder needs to be connected to the long-land die 5. Further according to the invention wherein the polymers of different elastic moduli are alternately fed, an electromagnetic valve or like valve mechanism (not shown) is provided, for example, at the outlet of each polymer feeder for controlling the discharge to be delivered to the confluent portion 3. In the case where extruders are used as means for alternately feeding the polymers, it is useful, for example, to control the extruder screws under a program to alternately discontinue the rotation thereof.

In addition to the first and second polymers, a polymer for forming a skin layer may be continuously fed to the outermost layer of the charge within the die to more effectively diminish variations in the outside diameter of the elongated body to be extruded. The extrudate then obtained has an inner layer formed by the polymers of different elastic moduli as arranged alternately longitudinally thereof, and a skin layer formed as the outermost layer always by the same additional polymer. This results in the advantage that the variations in the outside diameter are reduced more effectively because the outermost layer is always prepared from the same material.

The polymer for the skin layer may be different from the first and second polymers but is preferably the same as one of these polymers of different elastic moduli in view of the compatibility with these polymers. This can be accomplished by continuously feeding the selected one of at least two polymers always in contact with the inner surface of the die while intermittently feeding at least one remaining polymer instead of alternately feeding the polymers as stated above for complete replacement. The means for feeding the polymers in this mode unlike the foregoing alternate feeding means is adapted to produce an elongated body of the elastic modulus changing type by forming the outermost layer of the body from the same material at all times, and forming the inner layer thereof from the polymer materials of different elastic moduli in varying ratios. When the two polymers are fed by this means, the elongated body obtained has, for example, a portion consisting entirely of the first polymer, another portion wherein the first polymer is present only in the outermost layer and the second polymer is present in the inner layer, and a medium portion wherein the first and second polymers are present respectively in approximate half amounts.

According to the invention, the polymer feeders may be connected directly to the inlet of the long-land die 5, whereas the confluent portion 3 shown in FIG. 1 may alternatively be provided therebetween as means for joining the two polymers together and as a common channel for the two polymers to flow therethrough into the die 5. For example when the first polymer is changed over to the second polymer for feeding, the confluent portion 3 provided serves as a location where the two polymers mix together. The two polymers can then be mixed together satisfactorily with ease to form an elastic modulus changing portion in the elongated body to be obtained.

The long-land die for use in the present invention can be a hollow tubular body made of metal or ceramic and having a desired inside diameter. Generally, such a tubular body has a tapered portion for giving an adjusted outside diameter, and a land portion for forming and cooling the charge. For example, the land portion comprises a plurality of undivided die members or divided die pieces which are circular or shaped otherwise in section and joined together, or is in the form of an integral long-land die having no joint. The dies thus constructed each have an advantage; the former die, even if clogged with the resin material, can be restored easily, while the latter which has no joint easily affords a smooth-surfaced extrudate. Alternatively, the die may comprise a common die having a tapered portion and a long-land die portion connected thereto.

The length of the long-land die is dependent on the finished outside diameter of the extrudate to be produced, specific heat of the material, extrusion temperature, cooling temperature, etc. Assuming that the finished outside diameter is d, the land portion length is 30d to 200d, preferably 70d to 150d. For example in the case of usual catheters for the human body, the finished outside diameter is about 0.5 mm to about 3 mm, so that the land portion length is suitably about 35 mm to about 450 mm. When having a land portion length in this range, the die is desirable because the polymers can be satisfactorily formed and cooled within the die and are extrudable with a good result.

With reference to FIG. 1, the long-land die 5 comprises a tapered portion 51 and a land portion 52. The land portion 52 has a forming zone for making the polymers fed in a molten state from the feeders 1, 2 into a tubular form of desired outside diameter, and a cooling zone for cooling the polymers to extrude the polymers while permitting them to retain the tubular form. In this case, the tapered portion 51 for constricting the combined charge of polymers to the desired outside diameter, and an inlet part of the land portion 52 provide the forming zone, and the remaining part serves as the cooling zone. For cooling, various means are usable such as an air cooling system and liquid cooling system. For example, it is suitable to provide a cooling pipe around the die for circulating a refrigerant therethrough. The cooling pipe may be provided around the land portion locally or over the entire length thereof.

The polymers are fed to the long-land die, for example, through a Y-shaped channel as seen in FIG. 1, or a T-shaped channel. When a multiplicity of polymer feeders are used, these feeders are arranged along an annular channel around the confluent portion to feed the respective polymers to the die via the channel. Although various feeding modes or means are thus usable, it is desirable to feed the first polymer along a straight line to the confluent portion and feed the second polymer and other polymers (if used) from around the confluent portion. In this mode, the first polymer is fed to the long-land die through a straight channel, and the second polymer is fed from around the straight channel. As the discharge of the first polymer is decreased in this arrangement, the second polymer can be delivered from around the first polymer in a gradually increasing proportion to vary the component ratio at an average rate. This readily realizes formation of a desired elastic modulus changing portion wherein the elastic modulus varies gradually.

According to the invention, the polymers are formed and cooled within the long-land die, which therefore needs to be provided with means for supplying a lubricant to the inner surface of the die for the polymers continuously fed to smoothly advance through the die and give a smooth-surfaced elongated body. It is most desirable that the lubricant be supplied to the the die inner peripheral wall so as to cover the entire surface thereof without any interruption. Any supplying means is usable insofar as the lubricant can be thereby supplied in this state. The lubricant can be supplied, for example, through a slit utilizing a minute clearance as at a joint in the die, or through a surface of porous metal or like porous body. Suitably usable as techniques relating to such means for supplying the lubricant and to the long-land die described are those disclosed in U.S. Pat. No. 3,928,525.

The location where the lubricant is to be supplied is not limited specifically provided that the lubricant can be applied continuously to the inner surface of the die. The supplying means can be disposed, for example, at the land portion inlet of the long-land die, at the inlet or an intermediate portion of the tapered portion thereof, or in the polymer channel extending to the die. Above all, it is desirable to dispose the supplying means at the inlet of the tapered portion which most readily permits supply of the lubricant to the die inner surface in a uniform thickness. The lubricant, although satisfactorily applicable usually when supplied from one location, may be supplied from a plurality of locations. For example, it is suitable to arrange the supplying means at the tapered portion inlet of the long-land die and at the approximate midportion of the land portion thereof.

The polymers to be used in the present invention are not limited specifically but include various polymers. Examples of useful polymers are ethylenepropylenediene copolymer and like elastomers, polyvinyl chloride and like low-crytalline organic high polymers, polyacetal, polyphenylene sulfide, nylons and like polyamides, polybutylene terephthalate and like polyesters, liquid-crystal high polymers, high-crystalline organic high polymers such as polypropylene, polybutene-1, poly-4-methylpentene-1 and like polyolefins, etc. At least two polymers of different types or same type, which differ in elastic modulus, especially in flexural modulus, and are highly compatible with each other, can be suitably selected from among these polymers for use.

In the case where the invention is applied to the production of medical catheters previously stated, examples of polymers useful for the flexible portion are polyurethane elastomer, polystyrene elastomer, polyester elastomer, polyamide elastomer, chlorinated polyethylene elastomer and like elastomer resins, polyvinyl chloride, polyethylene, ethylene-vinyl acetate copolymer, ethylene-ethyl acrylate copolymer, etc. Examples of polymers useful for the torque transmitting portion are thermotropic liquid crystal polymers and like liquid crystal polymers, polyethylene, polypropylene, polyvinyl chloride, polyamide, polyoxymethylene, polycarbonate, polybutylene terephthalate, polyphenylene sulfide, polyether sulfone, polyarylate, polyether ether ketone, polyamidoimide, polyether imide, etc. At least two of such polymers are usable in the form of a blend as adjusted to exhibit a desired flexural modulus. The polymers for the flexible portion and those for the torque transmitting portion may have incorporated therein a contrast medium, such as barium sulfate, bismuth oxide, bismuth subcarbonate, bismuth tungstate, gold, platinum, silver or tungsten, for the catheter to exhibit a contrast when exposed to X-rays.

The polymer for the flexible portion of the medical catheter is preferably one retaining an elastic modulus of 0.01 to 50 kgf/mm$^2$, especially 0.1 to 10 kgf/mm$^2$, when heated to the temperature of the body into which the catheter is to be inserted. The polymer for the torque transmitting portion is useful insofar as it is capable of transmitting a torque as required at the body temperature. However, preferable to use is a polymer which retains an elastic modulus in the range of 20 to 2000 kgf/mm$^2$, more preferably 50 to 500 kgf/mm$^2$, when heated to the body temperature.

The elastic moduli of the respective polymers to be alternately continuously fed to the long-land die for giving an elongated body according to the invention are in the torque transmitting portion/flexible portion ratio of 30 to 2, preferably 20 to 3. When the elastic modulus ratio is in this range, catheters can be obtained which have a satisfactory elastic modulus changing portion.

For the flexible portion to properly function when the catheter is inserted into the body, the polymer to be used preferably has a specified glass transition temperature close to the body temperature. It is desired that the polymer for the flexible portion have a glass transition temperature approximate to the body temperature, e.g., a glass transition temperature of 29.5° to 43.5° C., more preferably about 31.5° to about 39.5° C., for use in the human body. In this case, the polymer for the torque transmitting portion preferably has a glass transition temperature which is, for example, at least 10° C., more preferably at least 20° C., higher than the body temperature.

To render the catheter insertable into the body more smoothly and more improved in torque transmission characteristics, it is desired that a medium portion gently changing in elastic modulus be formed between the flexible portion and the torque transmitting portion by gradually changing the ratio of the two polymers forming the catheter at the portion thereof where one polymer is changed over to the other polymer, whereas the aforementioned conventional process of joining with adhesive or heat is unable to produce a catheter having such a medium portion. Further when the two materials are merely extruded from a mixing die as disclosed in the foregoing patent publication SHO 54-8036 (1979), it is substantially impossible to extrude the materials as mixed together in the desired mode wherein the component ratio between the materials gradually changes longitudinally of the extrudate.

According to the invention, however, the polymers of different elastic moduli are alternately continuously fed to the long-land die with the feed change-over time adjusted. This makes it possible to produce not only an elongated body having an elastic modulus which is altered stepwise but also an elongated body having a medium portion wherein the first polymer is changed over to the second polymer with the elastic modulus of the former gradually changed to the elastic modulus of the latter. The reason is thought to be attributable to the following. Although the first and second polymers are different from each other in characteristics and are used in the form of a mixture, the mixture is passed through the forming zone provided by a relatively long closed channel, i.e., by the long-land die, so that the passage through the long-land die suppresses the variation in the outside diameter of the mixture due to the difference in characteristics, further cooling and solidifying the mixture in this state.

When the catheter to be produced has a skin layer formed by the same polymer as one of the first and second polymers, it is desired to continuously feed the polymer for the flexible portion in contact with the die inner surface and to intermittently feed the polymer for the transmitting portion. With the catheter obtained by such polymer feeding means, the polymer providing the flexible portion also forms the outermost layer of the torque transmitting portion. The use of the same material for the entire outermost layer of the catheter greatly diminishes outside diameter variations due to the internal pressure of extrusion operation. The flexible portion polymer (soft material) covering the catheter in its entirety further has the advantage that the catheter causes no damage or injury to organs or blood vessels when inserted into the body.

Preferably, the two polymers to be used in the present invention are approximate to each other in melt viscosity to the greatest possible extent insofar as they are suited to the use of the elongated body to be produced. For the different polymers to form a satisfactory mixture in the aforementioned portion wherein one polymer is changed over to the other polymer, it is desired that the two polymers be in match in melt viscosity at the extrusion temperature to the greatest possible extent. More specifically, the melt viscosity ratio between the two polymers is preferably 1: up to 2, more preferably 1: up to 1.5. Generally when polymers of different physical properties are extruded, the resulting extrudate has varying outside diameters owing to a difference in coefficient of expansion at the die outlet which difference is attributable chiefly to a difference in melt viscosity. The production process of the present invention encounters no problem when treating polymers of different melt viscosities since the polymers are formed and cooled within the long-land die, whereas an elongated body of more uniform outside diameter can be obtained with greater ease advantageously by selecting polymers which are approximate in melt viscosity to the greatest possible extent so as to obviate the cause of outside diameter variations.

Although various lubricants are usable for application to the inner surface of the long-land die, examples of suitable lubricants are silicone oils, glycol oils and the like. Especially desirable are those having the viscosity-temperature characteristics of 1 to $10^4$ cP at the temperature of the forming zone of the long-land die and $10^2$ to $10^6$ cP at room temperature. These lubricants are useful for smoothly passing the polymers through the die. More specific examples of such lubricants are dimethyl-silicone oils (e.g., "Toshiba Silicone Oil," brand name of Toshiba Silicone Co., Ltd., product designations TSF451 and YF-33), polyalkylene ether glycols (e.g., "Unilube," brand name of Nippon Oils & Fats Co., Ltd., product designations 75DE-2620 and 75DE-3800), etc.

It is desired that the combined rate of feed of the polymers to the long-land die be maintained at a constant value at all times even during the supply of one of the polymers or during a change-over to the other polymer. This makes it possible to more readily obtain an elongated body which is reduced in variations in outside and inside diameters and which has an elastic modulus changing portion with a more uniform rate of change in the component ratio between the two polymers.

The length of the elastic modulus changing portion is adjustable by varying the rate of replacement of one polymer by the other polymer. For example when a short modulus changing portion is to be obtained, the first polymer is fed to the long-land die at a rapidly decreasing rate while feeding the second polymer at a rapidly increasing rate to compensate for the decrease in the feed rate of the first polymer. Alternatively, a relatively long modulus changing portion can be prepared by feeding the first polymer to the long-land die at a moderately decreasing rate while similarly moderately increasing the feed rate of the second polymer. The modulus changing portion of the desired length can be obtained by suitably determining the rate of feed change-over to the other polymer in this way.

The outside diameter of the elongated body to be extruded can be determined most easily by varying the inside diameter of the long-land die. However, the outside diameter is adjustable by varying the rate of supply of the lubricant to the die inner surface since the extrusion operation is conducted while supplying& the lubricant thereto. The internal zone of the die for the polymers to pass through diminishes with an increase in the supply rate of lubricant, giving an elongated body with a diameter smaller than the inside diameter of the die. Thus, the latter method is advantageous for delicately adjusting the outside diameter of the elongated body to be extruded.

The process of the invention is also well suited to the production of hollow elongated bodies of the elastic modulus changing type, for example, catheters of this type. The catheter is a tubular medical instrument having a hollow channel (single lumen) or a plurality of channels (lumens, i.e., a multiple lumen). The lumens are utilized for liquid injection or discharge, insertion of an endoscopic image guide and illuminating light guide, or insertion of measuring instruments. Such an elongated body can be continuously produced by feeding the polymers to the long-land die along with a fluid for forming hollow portions, with the fluid enclosed in the polymer charge. With the fluid enclosed, the polymers pass through the die while holding the fluid therein, and are cooled and solidified in this state within the die and thereafter extruded into a hollow elongated body.

The fluid is enclosed before the polymers are fed to the long-land die. Although any fluid enclosing means is usable, it is suitable to dispose a fluid supply nozzle, for example, in the vicinity of the center of an intermediate channel extending from the polymer delivery portion to the inlet of the long-land die. In the case of the embodiment of FIG. 1, the fluid supply nozzle as directed toward the long-land die 5 is disposed in the polymer channel between the confluent portion 3 and the die 5. Preferably, the fluid is supplied toward the die without being allowed to spread out to the greatest possible extent. Catheters with a multilumen can be produced using a plurality of nozzles for forcing out the hollow portion forming fluid in a plurality of independent streams.

Examples of fluids usable are gases including air, nitrogen, oxygen, helium and carbon dioxide, and liquids including water, water-soluble liquids, silicone oil, glycol oil and like lubricants. Preferable among these are water-soluble liquids having a boiling point higher than the polymer extrusion temperature because of the advantages that they permit more stable extrusion than gases, can be discharged from the hollow portion of the resulting extrudate easily and allow the hollow portion to be readily washed for clearing compared with other liquids.

The diameter of the hollow portion is adjustable by controlling the rate of supply of the hollow portion forming fluid. An increase in the fluid supply rate increases the proportion of fluid occupying the interior of the long-land die, consequently forming a hollow portion of increased diameter. Conversely, if the supply rate is decreased, a hollow portion of reduced diameter can be obtained.

Figure 2:
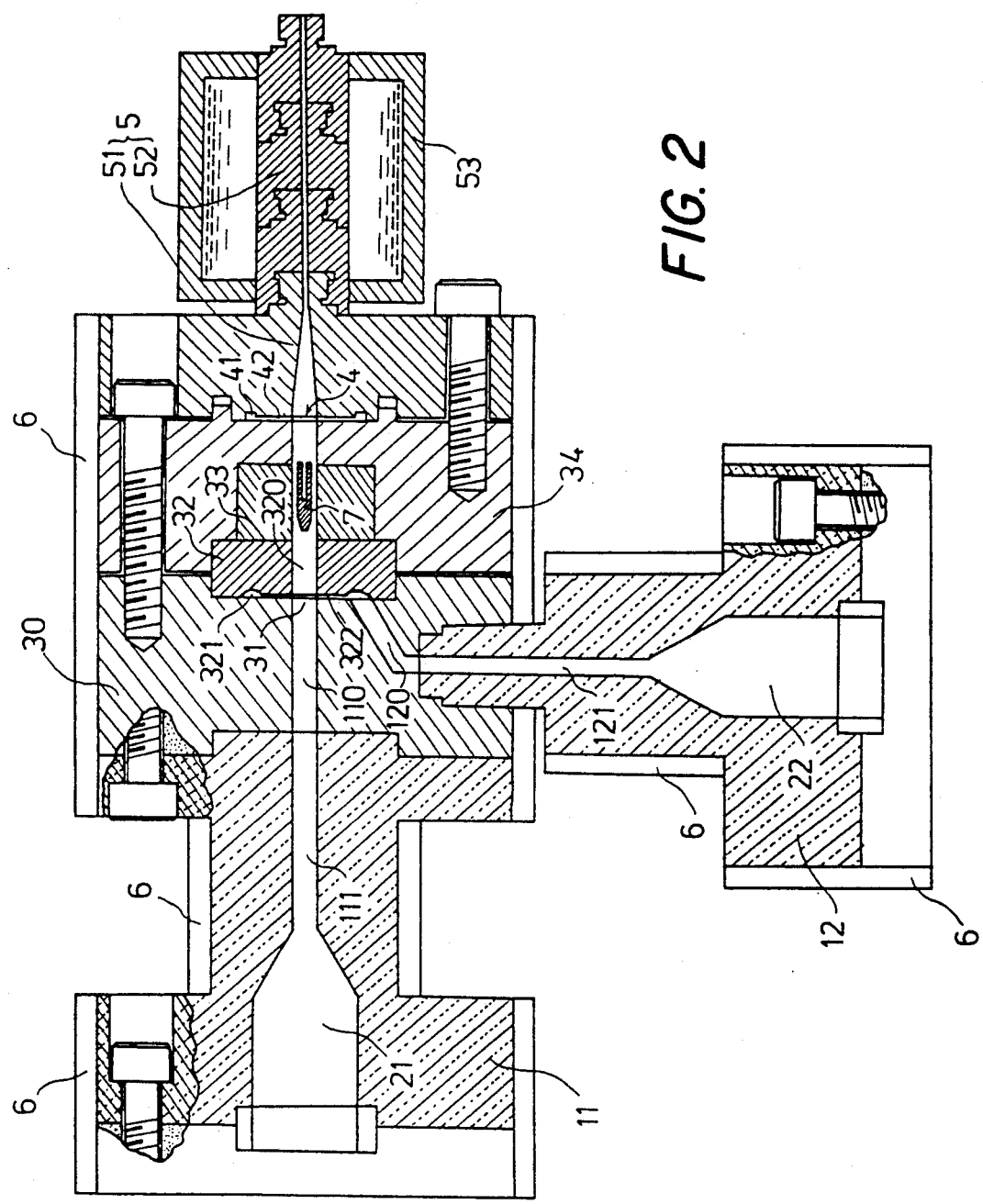
FIG. 2 is a sectional view showing a more specific example of apparatus for preparing an elongated body of the elastic modulus changing type by the process of the invention.

The present invention will be described below with reference to a specific embodiment. FIG. 2 is a sectional view showing the embodiment, i.e., a preferred apparatus for producing hollow elongated bodies of the elastic modulus changing type, such as catheters. The production process and apparatus of the invention will be described below with reference to the embodiment.

The drawing shows a first extruder adaptor 11 having connected thereto an unillustrated first extruder for extruding a first polymer 21 (hard material for the torque transmitting portion), and a second extrusion adaptor 12 having connected thereto an unillustrated second extruder for extruding a second polymer 22 (soft material for the flexible portion). These adaptors 11, 12 respectively have polymer passages 111, 121 which are in communication with a flow adaptor 32 providing a confluent portion 31 for the two polymers, by way of respective polymer channels 110, 120 formed in a flow section 30.

The channel 110 communicating with the first extruder is in communication with a channel 320 of the flow adaptor 32 in alignment therewith, while the channel 120 communicating with the second extruder is in communication with an annular groove 321 engraved in the flow adaptor 32 and centered about the channel 320. The annular groove 321 is in communication with the channel 320 through a disklike passage 322. Accordingly, the second polymer 22 is stored in the annular groove 321 first, and then supplied from around the channel 320 via the disklike passage 322.

The channel 320 is in communication with a tapered portion 51 of a long-land die 5 via a passage in a nipple 33 held by a nipple holder 34. The tapered portion 51 has an inlet which is provided with a lubricant applicator 4. The applicator 4 comprises an annular reservoir 41 for temporarily holding a lubricant and a disklike passage 42 communicating therewith. By an unillustrated plunger pump, gear pump or like pump adapted to supply a liquid at a constant rate under pressure, the lubricant is supplied to the annular reservoir 41 and caused to ooze through the disklike passage 42, whereby the lubricant is continuously supplied to the inner peripheral wall of the tapered portion 51.

The long-land die 5 has a land portion 52 which comprises divided die members joined together and one end of which is connected in series with the tapered portion 51. The land portion 52 is provided therearound with a cooling device comprising a hollow cylinder through which cooling water can be circulated.

A bandlike electric heater 6 is provided around each of the extruder adaptors 11, 12, flow section 30, nipple holder 34 and tapered portion 51. The polymer delivered from each extruder is maintained in a molten state with the heat of the heater 6 until the polymer reaches the long-land die 5. Instead of the electric heating system including the electric heaters, a high-frequency heating system, dielectric heating system or the like is alternatively usable.

Indicated at 7 is a hollow portion forming fluid feeder disposed in the passage through the nipple 33 and having a discharge outlet directed toward the direction of advance of polymers. Silicone oil or like hollow portion forming fluid is supplied by an unillustrated gear pump and discharged from the feeder 7.

Catheters of the elastic modulus changing type are produced by the apparatus of the present embodiment by the process to be described next. First, the screw (not shown) of the first extruder is rotated to extrude the polymer 21 for forming the torque transmitting portion, and the hollow portion forming fluid is discharged from the feeder 7 at the same time, whereby the first polymer 21 with the fluid enclosed therein is continuously fed toward the tapered portion 51. Since the tapered portion 51 and the land portion 52 are internally coated with the lubricant, the polymer 21 smoothly advances inside the die 5, cooled by the cooling device 53 and thereafter extruded.

After the polymer is fed from the first extruder for a predetermined period of time, the first extruder is stopped, and the screw of the second extruder is rotated at the same time always keeping constant the total amount of polymer fed, causing the second extruder to discharge the polymer 22 for the flexible portion. The second polymer 22 reaches the annular groove 321 of the flow adaptor 32 through the channel 120, is introduced into the confluent portion 31 via the disklike passage 322 and is now fed toward the tapered portion 51 in place of the first polymer 21. The polymer 22 is cooled in the land portion 52 and thereafter extruded like the polymer 21. When the screw of the second extruder is rapidly started with the screw of the first extruder rapidly brought to a stop in this procedure, a catheter can be obtained with a greatly changing elastic modulus, whereas if the stopping and starting are effected moderately, a catheter can be prepared which has a medium portion with a gradually changing elastic modulus.

While the second polymer 22 is being discharged, the first polymer 21 remains standing on the upstream side of the confluent portion 31 and is held in a molten state without solidifying by being heated with the heater 6. After the second polymer 22 has been discharged in a specified amount, the screw of the second extruder is stopped, while the screw of the first extruder is started, whereby the first polymer 21 standing on the upstream side of the confluent portion 31 is fed toward the tapered portion 51 again. At this time, the second polymer 22 remains standing in a molten state in the annular groove 321 of the flow adaptor 32.

Repeating the above cycle continuously extrudes a hollow elongated body wherein the different elastic moduli alternate longitudinally thereof. When thereafter cut at specified portions, the body provides a plurality of catheters of the elastic modulus changing type each having a torque transmitting portion and a flexible portion.

FIG. 3, (a) shows the catheter obtained by the above production process in section (lumens not shown). The first polymer (hard material) 21 entirely occupies the torque transmitting portion A of the catheter. In the medium portion B, the portion of first polymer 21 diminishes toward the center in a tapering fashion, while the portion of second polymer (soft material) 22 gradually increases from the outer periphery. The flexible portion C is made entirely of the second polymer 22. FIG. 3, (b), (c) and (d) show the torque transmitting portion A, the medium portion B and the flexible portion C, respectively, in cross section. Each lumen, i.e., hollow channel, is indicated at L.

The apparatus of the above embodiment is also adapted to produce catheters of the elastic modulus changing type which are provided over the entire length thereof with a skin layer made of the same material and formed as the outermost layer. In this case, the first polymer (hard material) 21 is first extruded from the first extruder into the channel 320, and at the same time, the second polymer (soft material) 22 is also discharged at a low rate from the second extruder into the channel 320 from therearound to form a torque transmitting portion having a thin layer of flexible portion polymer as the outermost layer. Subsequently, the first polymer 21 is fed at a gradually decreased rate while feeding the second polymer 22 at a gradually increased rate to compensate for the decrease and form a medium portion. Finally, the feed of the first polymer is discontinued while feeding the second polymer 22 only to form a flexible portion.

FIG. 4, (a) is a sectional view showing the catheter obtained by this process of production. In the torque transmitting portion A of the catheter, the outermost layer is formed by the second polymer 22, and the first polymer 21 is present inside thereof. The medium portion B and the flexible portion C are almost equivalent to the respective corresponding portions of the embodiment of FIG. 3 in the mode of two polymers present. FIG. 4, (b), (c) and (d) show the torque transmitting portion A, the medium portion B and the flexible portion C, respectively, in cross section.

Such a mode of feeding the polymers is desirable. Especially in forming the torque transmitting portion, it is desired to feed the polymers in such manner as to form the inner part providing partitioned lumens L by the first polymer 21 and to form the hollow cylindrical part around the inner part by the second polymer 22 as seen in FIG. 4,(b) showing the torque transmitting portion as occupied by the respective polymers. While the lumens L are formed by the fluid supplied by the abovementioned fluid feeder 7, this feeder 7 usually has connected thereto a tubular member which is termed a spider and which extends toward central portion of the channel 320. The spider is positioned across a clearance in the channel 320 around the fluid feeder 7 which is positioned in the center of the channel 320. The spider is therefore likely to impede the flow of polymer, which will in turn remain in the vicinity of the spider. If the polymers are fed in the complete change-over mode in this case as shown in FIG. 3, the preceding polymer partly remaining in the vicinity of the spider will be gradually forced forward despite a change-over, with the likelihood that the two polymers will become mixed together to form the outermost layer of the catheter to result in lower strength. The feeding mode shown in FIG. 4, (b) nevertheless eliminates this problem since the same polymer always flows in the vicinity of the spider.

With reference to FIG. 2, the second polymer is alternatively fed at a position downstream from the fluid feeder 7, especially downstream from the spider, as one of the preferred embodiments. The second polymer then flows without being impeded by the spider. This obviates the likelihood that a seam line in the remaining other polymer will be created if a flow of polymer passing around the spider joins the main flow again.

Although production examples wherein two polymers are used have been described above, it is of course possible to obtain elongated bodies of the elastic modulus changing type by extruding more than two kinds of polymers, for example, by using a multiplicity of flow adaptors as arranged for the channel 320.

EXAMPLES 1-10

Elongated bodies of the elastic modulus changing type and single-lumen and four-lumen catheters of the elastic modulus changing type which had the longitudinal section shown in FIG. 3, (a) were each prepared employing the production apparatus shown in FIG. 2 and described above, using the first polymer, second polymer, lubricant and hollow portion forming fluid listed in Table 1 and alternately feeding the two polymers in a complete change-over mode. The term "polymer change-over time" given in Table 1 refers to the time taken for the screw of the second (first) polymer extruder to become rotating at the rated speed after the screw of the first (second) polymer extruder started to stop.

The catheter of Example 6 was prepared under the same conditions as in Example 3 except that the time for a change-over from the first polymer to the second polymer was shortened (from 15 seconds to 2 seconds).

The elongated bodies obtained in Examples 1 to 10 were checked for the variation in the outside diameter by measuring the outside diameter of the portion prepared from the first polymer (torque transmitting portion), the outside diameter of the portion prepared from a mixture of the first and second polymers (medium portion) and the outside diameter of the portion prepared from the second polymer (flexible portion) and determining the maximum value of the differences between the measurements. Table 1 shows the production conditions involved and the outside diameter variations determined.

TABLE 1

|  | Example 1 | Example 2 | Example 3 | Example 4 | Example 5 |
|---|---|---|---|---|---|
| First polymer | Rigid PVC *2 | Rigid PVC *2 | Rigid PVC *2 | Polyurethane 1 *6 | Polyurethane 1 *6 |
| Extrusion temp. (°C.) | 170 | 170 | 170 | 185 | 185 |
| Melt viscosity *1 (P) | $2 \times 10^4$ | $2 \times 10^4$ | $2 \times 10^4$ | $1 \times 10^3$ | $1 \times 10^3$ |
| Elastic modulus (23° C., kg/mm$^2$) | 35 | 35 | 35 | 56 | 56 |
| Second polymer | Soft PVC *3 | Soft PVC *3 | Soft PVC *3 | Polyurethane 2 *7 | Polyurethane 2 *7 |
| Extrusion temp. (°C.) | 170 | 170 | 170 | 185 | 185 |
| Melt viscosity *1 (P) | $2 \times 10^4$ | $2 \times 10^4$ | $2 \times 10^4$ | $7 \times 10^4$ | $7 \times 10^4$ |
| Elastic modulus (23° C., | 0.5 | 0.5 | 0.5 | 0.2 | 0.2 |

TABLE 1-continued

| kg/mm² | | | | | | |
|---|---|---|---|---|---|---|
| Total discharge (cc/min) | | 1.9 | 1.9 | 1.9 | 1.6 | 2.1 |
| Long-land die | I.D. (mm) | 1.5 | 3.0 | 1.5 | 2.3 | 2.3 |
| Forming zone | Length (mm) | 35 | 35 | 35 | 35 | 35 |
| | Temp. t1 (°C.) | 170 | 170 | 170 | 185 | 185 |
| Cooling zone | Length (mm) | 90 | 70 | 90 | 60 | 60 |
| | Temp. t2 (°C.) | 20 | 20 | 20 | 20 | 20 |
| Lubricant | | Glycol oil *4 | Glycol oil *4 | Glycol oil *4 | Silicone oil *5 | Silicone oil *5 |
| Supply rate (cc/min) | | 0.1 | 0.1 | 0.1 | 0.05 | 0.05 |
| Melt viscosity at t1 (cP) | | 1000 | 1000 | 1000 | 1200 | 1200 |
| Melt viscosity at t2 (cP) | | 40000 | 40000 | 40000 | 10000 | 10000 |
| Hollow portion forming fluid | | — | Silicone oil *5 | Glycol oil *4 | — | Silicone oil *5 |
| Supply rate (cc/min) | | — | 1.68 | 1.0 | — | 0.05 |
| Melt viscosity at t1 (cP) | | — | 1500 | 1000 | — | 1200 |
| Melt viscosity at t2 (cP) | | — | 10000 | 40000 | — | 10000 |
| Shape in cross section | | Solid | Four lumens | Single lumen | Solid | Four lumens |
| Polymer change-over time (sec) | | 15 | 20 | 15 | 15 | 8 |
| Length (cm) of modulus changing portion | | 27 | 17 | 41 | 23 | 12 |
| O.D. variation (mm) at joint of first and second polymers | | 0.05 | 0.1 | 0.05 | 0.07 | 0.1 |

| | | Example 6 | Example 7 | Example 8 | Example 9 | Example 10 |
|---|---|---|---|---|---|---|
| First polymer | | Rigid PVC *2 | Polypropylene *8 | High-density PE *10 | Polystyrene *12 | PVC *14 |
| Extrusion temp. (°C.) | | 170 | 200 | 190 | 170 | 170 |
| Melt viscosity *1 (P) | | 2 × 10⁴ | 3 × 10³ | 8.5 × 10³ | 6.0 × 10³ | 3 × 10⁴ |
| Elastic modulus (23° C., kg/mm²) | | 35 | 105 | 105 | 50 | 40 |
| Second polymer | | Soft PVC *3 | Polyethylene *9 | EMA *11 | Polystyrene *13 | PVC *15 |
| Extrusion temp. (°C.) | | 170 | 200 | 190 | 190 | 170 |
| Melt viscosity *1 (P) | | 2 × 10⁴ | 3 × 10³ | 8.5 × 10³ | 6.0 × 10³ | 3 × 10⁴ |
| Elastic modulus (23° C., kg/mm²) | | 0.5 | 16 | 6.8 | 0.3 | 2.0 |
| Total discharge (cc/min) | | 1.9 | 1.5 | 1.5 | 1.9 | 1.9 |
| Long-land die | I.D. (mm) | 1.5 | 1.5 | 2.0 | 2.0 | 1.5 |
| Forming zone | Length (mm) | 35 | 35 | 35 | 35 | 35 |
| | Temp. t1 (°C.) | 170 | 200 | 200 | 190 | 240 |
| Cooling zone | Length (mm) | 90 | 90 | 90 | 90 | 90 |
| | Temp. t2 (°C.) | 20 | 20 | 70 | 20 | 120 |
| Lubricant | | Glycol oil *4 | Glycol oil *4 | Glycol oil *4 | Silicone oil *5 | Glycol oil *4 |
| Supply rate (cc/min) | | 0.1 | 0.1 | 0.15 | 0.15 | 0.15 |
| Melt viscosity at t1 (cP) | | 1000 | 1000 | 1000 | 1100 | 600 |
| Melt viscosity at t2 (cP) | | 40000 | 40000 | 5000 | 10000 | 1800 |
| Hollow portion forming fluid | | Glycol oil *4 | Silicone oil *5 | Glycol oil *4 | Silicone oil *5 | Glycol oil *4 |
| Supply rate (cc/min) | | 1.0 | 1.5 | 1.2 | 1.0 | 1.2 |
| Melt viscosity at t1 (cP) | | 1000 | 800 | 1000 | 1100 | 600 |
| Melt viscosity at t2 (cP) | | 40000 | 10000 | 5000 | 10000 | 1800 |
| Shape in cross section | | Single lumen | Single lumen | Four lumens | Single lumen | Four lumens |
| Polymer change-over time (sec) | | 2 | 15 | 20 | 20 | 20 |
| Length (cm) of modulus changing portion | | 1 | 28 | 27 | 28 | 50 |
| O.D. variation (mm) at joint of first and second polymers | | 0.08 | 0.05 | 0.12 | 0.05 | 0.1 |

Notes to Table 1
The elastic modulus in the table is modulus in tension when the polymer is polyvinyl chloride, or flexural modulus if otherwise.
*1 Melt viscosity when the rate of shear is 3 × 10² (l/sec) at the extrusion temperature.
*2 Esmedica V 1330E (brand name of Sekisui Chemical Co., Ltd.)
*3 Esmedica V 4142E (brand name of Sekisui Chemical Co., Ltd.)
*4 Unilube 75DE-2620 (brand name of Nippon Oils & Fats Co., Ltd.)
*5 Toshiba Silicone Oil YF-33 (brand name of Toshiba Silicone Co., Ltd.)
*6 Ether-type polyurethane which is a mixture of 20 parts by weight of Diary MM2500 (brand name of Mitsubishi Heavy Industries, Ltd.) and 80 parts by weight of nonaromatic liquid crystal polymer E310 (brand name of Mitsubishi Chemical Industries, Ltd.)
*7 Ether-type polyurethane, Diary MM2500 (brand name of Mitsubishi Heavy Industries, Ltd.)
*8 Mitsubishi Polypropylene MA4 (brand name of Mitsubishi Petrochemical Co., Ltd.)
*9 Mitsubishi Polyethylene-LD EH30 (brand name of Mitsubishi Petrochemical Co., Ltd.)
*10 Mitsubishi Polyethylene-HD HY540 (brand name of Mitsubishi Petrochemical Co., Ltd.)
*11 Mitsubishi Yukalon EMA XG-300E (brand name of Mitsubishi Petrochemical Co., Ltd.)
*12 Asaflex 815 (brand name of Asahi Chemical Industry Co., Ltd.)
*13 Tufprene 315 (brand name of Asahi Chemical Industry Co., Ltd.)
*14 Esmedica V 133BE-B30, containing 30 wt. % of BaSO₄, contrast medium (brand name of Sekisui Chemical Co., Ltd.)
*15 Esmedica V 414BE-B30, containing 30 wt. % of BaSO₄, contrast medium (brand name of Sekisui Chemical Co., Ltd.)

EXAMPLES 11 AND 12

Four-lumen catheters of the elastic modulus changing type having the longitudinal section shown in FIG. 4, (a) were each prepared employing the production apparatus shown in FIG. 2 and described above, using the first polymer, second polymer, lubricant and hollow portion forming fluid listed in Table 2, feeding the second polymer always in contact with the inner surface of the long-land die and intermittently feeding the first polymer.

The catheters obtained in Examples 11 and 12 were checked for the variation in the outside diameter in the same manner as above by measuring the outside diameter of the torque transmitting portion, the outside diameter of the medium portion and the outside diameter of the flexible portion and determining the maximum value of the differences between the measurements. Table 2 shows the production conditions involved and the outside diameter variations determined.

TABLE 2

|  | Example 11 | Example 12 |
|---|---|---|
| First polymer | Rigid PVC *2 | High-density PE *10 |
| Extrusion temp. (°C.) | 170 | 190 |
| Melt viscosity *1 (P) | $2 \times 10^4$ | $8.5 \times 10^3$ |
| Elastic modulus (23° C., kg/mm²) | 35 | 105 |
| Second polymer | Soft PVC *3 | EMA *11 |
| Extrusion temp. (°C.) | 170 | 190 |
| Melt viscosity *1 (P) | $2 \times 10^4$ | $8.5 \times 10^3$ |
| Elastic modulus (23° C., kg/mm²) | 2.0 | 6.8 |
| Total discharge (cc/min) | 1.9 | 1.5 |
| Long-land die I.D. (mm) | 2.0 | 2.0 |
| Forming zone Length (mm) | 35 | 35 |
| Forming zone Temp. t1 (°C.) | 240 | 200 |
| Cooling zone Length (mm) | 90 | 90 |
| Cooling zone Temp. t2 (°C.) | 120 | 20 |
| Lubricant | Glycol oil *4 | Glycol oil *4 |
| Supply rate (cc/min) | 0.15 | 0.15 |
| Melt viscosity at t1 (cP) | 600 | 1000 |
| Melt viscosity at t2 (cP) | 1800 | 40000 |
| Hollow portion forming fluid | Glycol oil *4 | Glycol oil *4 |
| Supply rate (cc/min) | 1.2 | 1.2 |
| Melt viscosity at t1 (cP) | 600 | 1000 |
| Melt viscosity at t2 (cP) | 1800 | 40000 |
| Shape in cross section | Four lumens | Four lumens |
| Polymer change-over time (sec) | 20 | 20 |
| Length (cm) of modulus changing portion | 27 | 27 |
| Thickness (mm) of second polymer layer in torque transmitting portion | 0.15 | 0.15 |
| O.D. variation (mm) at joint of first and second polymers | 0.05 | 0.05 |

COMPARATIVE EXAMPLES 1 AND 2

For comparison with Examples given above, elongated bodies were prepared using the same polymers, lubricant and hollow portion forming fluid as in Examples 1 and 2, employing the apparatus of FIG. 2 except the long-land die thereof (i.e., with the land portion 52 removed to extrude the charge directly from the tapered portion 51, the die outlet diameter being the same as in the examples) and alternately feeding the polymers in the same manner as in Examples 1 to 10. The elongated bodies obtained were checked for variations in the outside diameter in the same manner as in the foregoing examples. Table 3 shows the results.

TABLE 3

|  | Comparative Example 1 | Comparative Example 2 |
|---|---|---|
| First polymer | Rigid PVC *2 | Rigid PVC *2 |
| Extrusion temp. (°C.) | 170 | 170 |
| Melt viscosity *1 (P) | $2 \times 10^4$ | $2 \times 10^4$ |
| Elastic modulus (23° C., kg/mm²) | 35 | 35 |
| Second polymer | Soft PVC *3 | Soft PVC *3 |
| Extrusion temp. (°C.) | 170 | 170 |
| Melt viscosity *1 (P) | $2 \times 10^4$ | $2 \times 10^4$ |
| Elastic modulus (23° C., kg/mm²) | 0.5 | 0.5 |
| Total discharge (cc/min) | — | — |
| Long-land die I.D. (mm) | — | — |
| Forming zone Length (mm) | — | — |
| Forming zone Temp. t1 (°C.) | — | — |
| Cooling zone Length (mm) | — | — |
| Cooling zone Temp. t2 (°C.) | — | — |
| Lubricant | Glycol oil *4 | Glycol oil *4 |
| Supply rate (cc/min) | 0.1 | 0.15 |
| Melt viscosity at t1 (cP) | 1000 | 1000 |
| Melt viscosity at t2 (cP) | 40000 | 40000 |
| Hollow portion forming fluid | — | Silicone oil *5 |
| Supply rate (cc/min) | — | 1.68 |
| Melt viscosity at t1 (cP) | — | 1500 |
| Melt viscosity at t2 (cP) | — | 10000 |
| Shape in cross section | Solid | Four lumens |
| Polymer change-over time (sec) | 15 | 20 |
| Length (cm) of modulus changing portion | 27 | 17 |
| O.D. variation (mm) at joint of first and second polymers | 0.32 | Not formable |

The comparison of Tables 1 and 2 with Table 3 reveals the following. The elongated bodies of Examples were very small in outside diameter variations and almost free of variations in the outside diameter. In contrast, the products of Comparative Examples had marked variations in the outside diameter which were even observable with the unaided eye. Further when the products of Examples having a lumen or lumens were cut and checked for variations in the inside diameter, the variations were all not greater than 0.05 mm although not shown in the tables.

As described above, the process and apparatus of the present invention provide elongated bodies of the elastic modulus changing type having no variations in the outside diameter even with use of polymers which are different in elastic modulus, extrusion characteristics and swelling characteristics and which are alternately extruded. Hollow elongated bodies can also be obtained which have no inside diameter variation.

Accordingly, the present process readily affords elongated bodies of the elastic modulus changing type with a uniform outside diameter although such bodies are in no way available by the conventional production processes, and is well suited to the production of hollow elongated bodies, such as catheters, which need to have extremely accurate inside and outside diameters. The process is adapted to continuously produce elongated bodies which differ in elastic modulus longitudinally thereof and is therefore favorable for the quantity production of catheters of high quality. Further according to the invention, the polymers are cooled within the long-land die and thereafter extruded into an elongated body as already cooled and solidified, so that the invention has another advantage that the elongated body as extruded is easy to handle.

What is claimed is:

1. A process for producing an elongated polymeric body of an elastic modulus changing type said process comprising:
    a first step of continuously feeding an amount of a first polymer to a long-land die having a forming zone in an inlet portion and a cooling zone in an outlet portion, the die having an inner surface supplied with a lubricant, a second step of continuously feeding an amount of the first polymer at a first feeding rate and an amount of a second polymer which has an elastic modulus different from the elastic modulus of the first polymer at a second feeding rate to the long-land die, under conditions where the second feeding rate of the second polymer gradually increases and the first feeding rate of the first polymer gradually decreases while the sum of the amount of the first polymer and the amount of the second polymer is constant, so as to form mixtures of the first polymer and the second polymer, a third step of continuously feeding an amount of the second polymer to the long-land die.

2. A process as defined in claim 1 wherein in addition to said first and second polymers, a skin layer polymer is continuously fed to the outermost layer of the polymers within the die.

3. A process as defined in claim 2 wherein the skin layer polymer is the same as one of said first and second polymers which are different in elastic modulus.

4. A process as defined in claim 1 wherein the polymers of different elastic moduli have a melt viscosity ratio therebetween of 1: up to 2.

5. A process as defined in claim 1 wherein the combined rate of feed of said first and second polymers to the long-land die is constant at all times.

6. A process as defined in claim 1 wherein means is used for adjusting the rate of change-over from one of the polymers to the other polymer for feeding to the long-land die to thereby form an elastic modulus changing portion of controlled length in the elongated body to be extruded.

7. A process as defined in claim 1 wherein the outside diameter of the elongated body to be extruded is adjusted by controlling the rate of supply of the lubricant to the long-land die.

8. A process as defined in claim 1 wherein a fluid for forming a hollow portion is supplied to the long-land die together with the polymer to be fed with the fluid enclosed in the polymer.

9. A process as defined in claim 8 wherein the fluid is water or a water-soluble liquid.

10. A process as defined in claim 8 wherein the diameter of the hollow portion is adjusted by controlling the rate of supply of the fluid.

11. An apparatus for producing an elongated polymeric body of an elastic modulus changing type, the apparatus comprising a first extruder for feeding a first polymer having an elastic modulus, a second extruder for feeding a second polymer having an elastic modulus different from the elastic modulus of the first polymer, a long-land die connected to the first extruder and the second extruder, said long-land die having forming zone for forming polymers fed thereto into an outer body and a cooling zone for solidifying polymers formed in the forming zone, said cooling zone having a function for cooling the polymers until the cooling substantially becomes unnecessary after the polymer are extruded out of the long-land die, means for alternately feeding polymers from the first and second polymer extruders to the long-land die, and means for supplying a lubricant to inner surface of the long-land die.

12. An apparatus as defined in claim 11 wherein confluent means is provided for joining together the polymers discharged from the respective polymer feeding means, and the polymers are fed to the long-land die through the confluent means.

13. An apparatus as defined in claim 12 wherein the lubricant supplying means is disposed between the confluent means and the long-land die.

14. An apparatus as defined in claim 12 wherein the confluent means has a confluent channel, one of the polymers is supplied to the confluent channel in alignment therewith, and the other polymer or polymers are supplied to the confluent channel from therearound.

15. An apparatus as defined in claim 12 wherein the long-land die is provided at an inlet portion thereof with an outside diameter adjusting portion having a tapered inner peripheral wall for adjusting the outside diameter of the elongated body to be produced.

16. An apparatus as defined in claim 12 wherein fluid supply means for enclosing a fluid in the polymers is provided in a polymer channel between the confluent means and the long-land die.

17. An apparatus as defined in claim 16 wherein the fluid supply means has a plurality of nozzles.

* * * * *